United States Patent [19]

Ban et al.

[11] 4,403,039

[45] Sep. 6, 1983

[54] METHOD AND APPARATUS FOR ANALYSIS OF IONIC SPECIES

[75] Inventors: Tsuyoshi Ban; Takeshi Murayama; Setsuo Muramoto; Yuzuru Hanaoka, all of Musashino, Japan

[73] Assignee: Yokogawa Hokushin Electric Works, Tokyo, Japan

[21] Appl. No.: 309,905

[22] Filed: Oct. 9, 1981

[30] Foreign Application Priority Data

Oct. 29, 1980 [JP] Japan .............................. 80-151554
Oct. 29, 1980 [JP] Japan .............................. 80-151555

[51] Int. Cl.³ ................. G01N 31/04; G01N 31/06; G01N 33/20
[52] U.S. Cl. ................. 436/150; 210/198.2; 210/656; 210/662; 436/80; 436/81; 422/70
[58] Field of Search ............. 210/635, 638, 644, 656, 210/662, 663, 746, 806, 195.2, 257.2, 294, 321 R, 321 A, 321 B, 433.2; 422/68, 70, 81, 101; 23/230 R

[56] References Cited

U.S. PATENT DOCUMENTS

| | | | |
|---|---|---|---|
| 3,342,729 | 9/1967 | Strand | 210/638 |
| 3,399,972 | 9/1968 | Skeggs et al. | 210/321.2 |
| 3,450,508 | 6/1969 | Cooper et al. | 210/321.2 |
| 3,920,397 | 11/1975 | Small et al. | 23/230 R |

Primary Examiner—Michael S. Marcus
Attorney, Agent, or Firm—Parmelee, Bollinger & Bramblett

[57] ABSTRACT

A method of analyzing a sample solution containing an ionic species of interest paired with an ionic species of the opposite sign comprises introducing the sample solution into a separation column with an eluant solution, introducing an eluate from the separation column into the inner passage of a diffusion type deionizer of the double tubular construction which is defined by a tube of an ion exchange composition, while a scavenger solution is introduced into the outer passage of the deionizer in a direction of flow opposite to that of the eluate in the inner passage, whereby the ionic species of the opposite sign is removed from the eluate into the scavenger solution, and measuring the electric conductivity of the eluate from the deionizer to thereby determine the concentration of the ionic species of interest in the sample solution. An apparatus for carrying out this method is also disclosed.

8 Claims, 12 Drawing Figures

METHOD AND APPARATUS FOR ANALYSIS OF IONIC SPECIES

BACKGROUND OF THE INVENTION

This invention relates to a method and apparatus for he analysis of anions or cations in a sample solution by on chromatography.

The term "ion chromatography" designates the high-speed chromatography directed chiefly to inorganic ons which was published by H. Small et al in 1975 Anal. Chem., 47, 1801 (1975)].

Ion chromatography has already been reduced to practice and has been finding extensive utility in applications to various forms of microanalysis such as analysis of ecological specimens and organic specimens, control and analysis of various processes, and elementary analysis.

FIG. 1 is an explanatory diagram illustrating the process flow in a conventional ion chromatograph adapted for the analysis of anions.

In FIG. 1, the ion chromatograph is seen to be provided with an eluant solution reservoir 1 for storing NaOH to be used as an eluant solution, a pump 2 for transferring the eluant solution of the reservoir 1 under pressure to a sample injection valve 3, which is adapted to collect a prescribed amount of the sample solution and transfer the collected sample solution with the eluant solution to a separation column 4 packed with a resin formed by electrostatically bonding an anion-exchange resin to a cation-exchange resin so as to function jointly as an anion-exchange resin and adapted to separate various ionic species from the influent liquid, a background separation column 5 (hereinafter referred to as BSC for short) packed with a strongly acidic cation-exchange resin and adapted to capture ions from the eluant solution, and a conductivity meter 6 adapted to introduce the liquid discharged from BSC 5 into the cell thereof and measure the conductivity of the liquid.

The problems encountered by the ion chromatograph of the construction described above originate in the BSC.

One of the problems is that under the ordinary conditions of analysis, the operation for regeneration of the BSC should be completed in 8 to 10 hours. The BSC is used herein for the purpose of capturing the ions present in the eluant solution, diminishing the background of such ions of the eluant solution on the conductivity meter, and enhancing the sensitivity of the detection of ions of interest. With the elapse of time, however, the BSC gradually loses its functioning ability. This is due to the reaction of the formula (1) shown below proceeding within the column and, consequently, the ion-exchange resin is converted from the H form to the Na form.

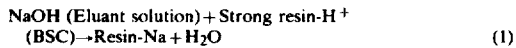

NaOH (Eluant solution) + Strong resin-H+
(BSC)→Resin-Na + H₂O     (1)

When the whole ion-exchange resin is converted to the Na form, the reaction of the formula (1) no longer continues. Consequently, the base line in the conductivity meter rises and, at the same time, the amplifying function upon the anions is lost. The conventional ion chromatograph, therefore, has been designed so that the function of the BSC is regenerated at fixed intervals by supplying of 1 N—3 N HCl to the BSC. Of course, the fixed intervals for this regeneration may possibly be shortened to 1 to 2 hours under such conditions of analysis which necessitate a highly concentrated eluant solution to be supplied in a high flow volume.

Another problem is that the peak form is impaired when the liquid eluted from the separation column is passed through the BSC. This decay of the peak form is ascribable to the fact that the BSC is formed by packing a tubule measuring 3 to 6 mm in inside diameter and 25 to 50 cm in length with an ion-exchange resin.

The prior art has been described with reference to an ion chromatograph designed for the analysis of anions. The conventional ion chromatograph used for the analysis of cations has substantially the same basic process flow and suffers similarly from the problems arising in the BSC.

SUMMARY OF THE INVENTION

It is an object of this invention to overcome the drawbacks of the prior art as hereinabove pointed out, and provide a method of, and an apparatus for analyzing an ionic species of a particular sign which can remove an ionic species of the opposite sign from an eluate from a separation column without requiring any regeneration of the deionizer composition, and without destroying the peak form of the ionic species of interest.

According to this invention, this object is attained by employing a diffusion type deionizer of the double tubular construction having an inner passage defined by a tube of an ion exchange composition. The eluate is introduced from the separation column into the inner passage of the deionizer, while a scavenger solution is caused to flow through the outer passage of the deionizer in a direction opposite to the flow of the eluate in the inner passage, whereby the ionic species of the opposite sign is removed from the eluate. The eluate is, then, introduced into the cell of a conductivity meter.

DESCRIPTION OF THE PREFERRED EMBODIMENTS

This invention will be described in detail below with reference to the accompanying drawings.

Figure 1:
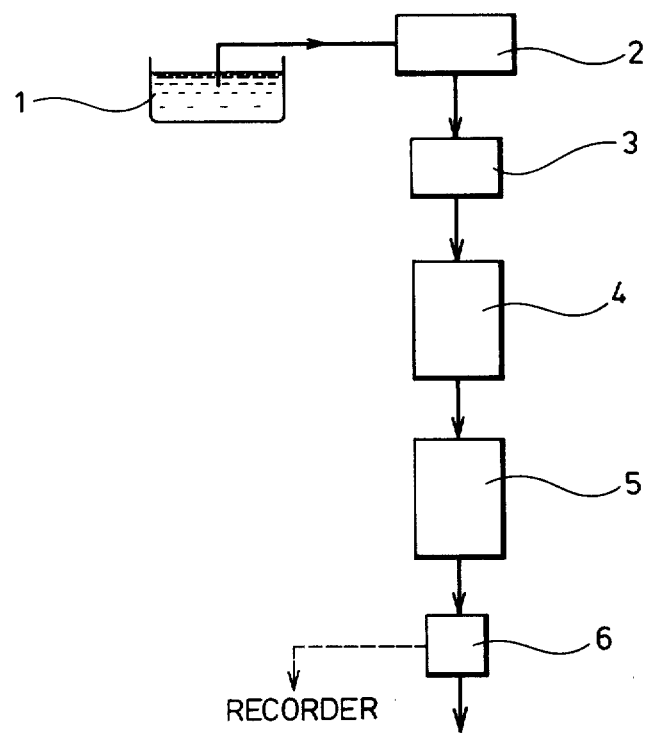
FIG. 1 is an explanatory diagram illustrating the construction of flow paths in the conventional ion chromatograph.
Figure 2:
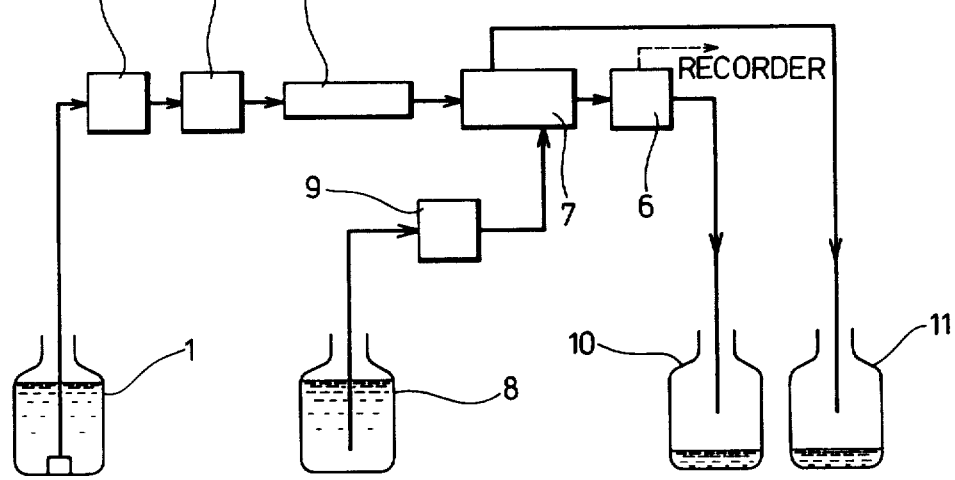
FIG. 2 is an explanatory diagram illustrating the construction of a typical analytical apparatus according to the present invention.

FIG. 2 is an explanatory diagram illustrating the construction of a typical analytical apparatus according to the present invention. More specifically, it is an explanatory diagram illustrating the construction of an ion chromatograph for the analysis of anions in a sample solution.

The analytical apparatus of FIG. 2 comprises an eluant solution reservoir 1 for storing an alkaline eluant solution such as, for example, 0.002 N NaOH, a pump 2 for transfering under pressure the eluant solution in the reservoir 1 under pressure to a sample injection means 3 for transferring a sample solution injected in a prescribed amount into the flow path with the aid of a microsyringe, in conjunction with the eluant solution from the pump 2, to a separation column 4, the separation column 4 packed with a strongly basic anion-exchange resin having a low ion-exchange capacity, a diffusion type decationizer means 7 formed of an eluant solution compartment and a scavenger solution compartment which share a common wall formed of a cation-exchange composition, a scavenger solution reservoir 8 for storing a scavenger solution such as, for example, 0.1 N HCl (or HNO₃), a pump 9 for transferring under pressure the scavenger solution of the reservoir 8 to the scavenger solution compartment in the decationizer means 7, a conductivity meter 6 for receiving the effluent from the eluate solution compartment of the decationizer means 7 into the cell thereof, measuring the conductivity therein, and displaying the signal representing the conductivity for example on a recorder, a reservoir 10 for storing the solution which has undergone the measurement in the conductivity meter 6, and a reservoir 11 for storing the scavenger solution flowing out of the decationizer means 7.

Now, the construction of the decationizer means 7 will be described in detail with reference to FIG. 3A and FIG. 3B.

Figure 3A:
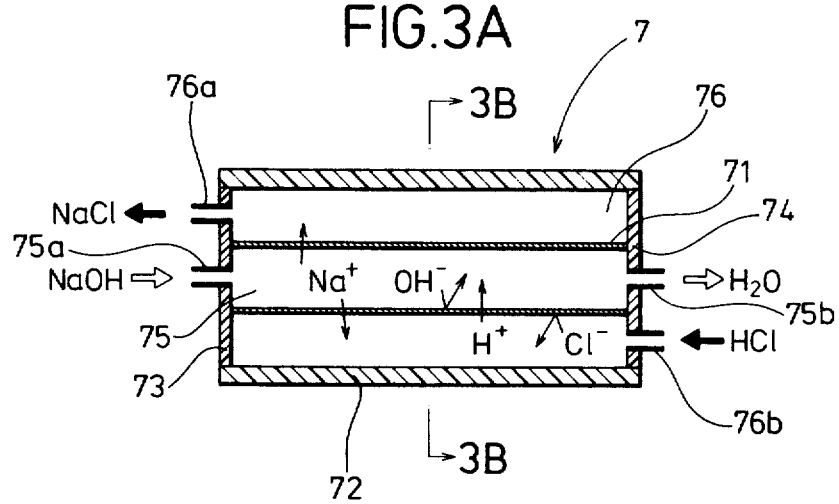
FIG. 3A is an explanatory diagram illustrating the construction of a diffusion type decationizer means using a cation-exchange composition in the typical analytical apparatus of the present invention.
Figure 3B:
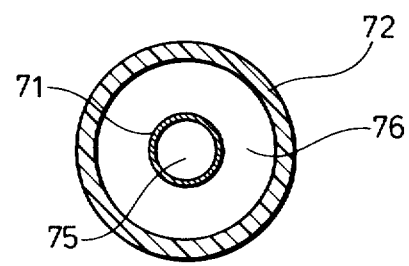
FIG. 3B is a cross sectional view along the line 3B—3B of FIG. 3A.

FIG. 3 depicts the construction of the decationizer means; FIG. 3A representing a cross section of the means in its axial direction and FIG. 3B representing a cross section taken along the line 3B—3B in the diagram of FIG. 3A.

The means 7 has a construction wherein a two-wall tube is formed by using a tube 72 of stainless steel enclosing therein a tube 71 of a cation-exchange composition and interposing a suitable tubular space between the two tubes 71 and 72. The opposite open ends of the two-wall tube are closed with lids 73 and 74 to give rise therein to an eluant solution compartment 75 and a scavenger solution compartment 76, and holes 75a, 75b, 76a, and 76b are formed to establish communication between the interiors of the compartments and the ambient air. The liquid eluted from the separation column 4 flows in the direction of from the hole 75a via the compartment 75 to the hole 75b. The scavenger solution delivered under pressure by the pump 9 flows in the direction of from the hole 76b via the compartment 76 to the hole 76a. The direction of the flow of the eluant solution and that of the flow of the scavenger solution are opposite.

Now, the operation of the analytical apparatus having the aforementioned construction will be described.

The eluant solution, 0.002 N NaOH, is forwarded by the pump 2 in a flow volume of about 2.0 ml/min. through the sample injection device 3, the separation column 4, the eluant solution compartment 75 of the decationizer means 7, and the cell of the conductivity meter 6 to the reservoir 10. Separately, the scavenger solution, 0.1 N HCl, is forwarded by the pump 9 in a flow volume of about 1 ml/min. from the scavenger solution compartment 76 to the reservoir 11.

Figure 5:
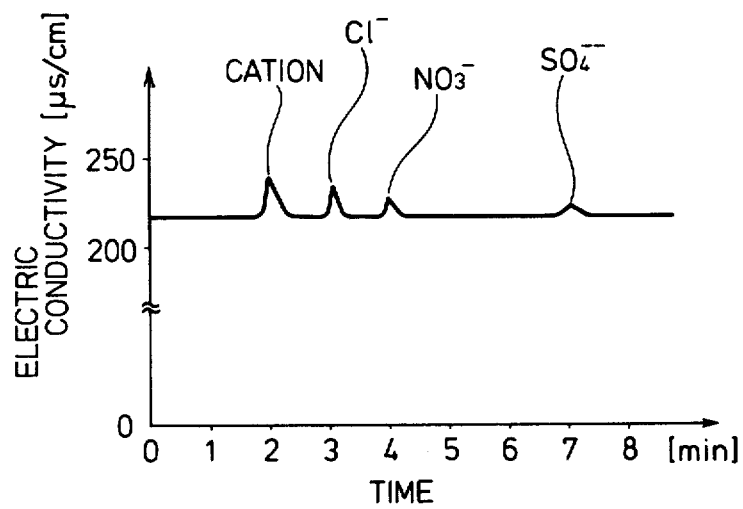
FIG. 5 is a diagram showing a typical chromatogram of the effluent at the outlet of the separation column in the typical ion chromatograph for the analysis of anions according to the present invention.

Now, at the sample injection device 3, 100 μl of a sample solution containing the ionic species of 100 mg/liter (ppm) of $Cl^-$, 100 mg/liter (ppm) of $NO_3^-$, and 100 mg/liter (ppm) of $SO_4^{2-}$ is injected into the flow of the eluant solution and delivered to the separation column 4. The ionic species are separated in the separation column 4. The chromatogram of the solution at the outlet of the separation column 4 is as shown in FIG. 5. In the chromatogram, with the conductivity, about 210 μs/cm, of the 0.002 N NaOH as the base line, the cation ($Na^+$ where the ion paired with the anion of interest is Na or $K^+$ where the ion is K), and the anions $Cl^-$, $NO_3^-$, and $SO_4^{2-}$ appear in the order mentioned. Actually, the ionic species are bonded with the $Na^+$ in the eluant solution so that $Cl^-$ exists as NaCl, $NO_3^-$ as $NaNO_3$, and $SO_4^{2-}$ as $Na_2SO_4$ respectively. Since these salts are eluted out as contained in the 0.002 N NaOH, the change of conductivity at the peak of $Cl^-$, for example, is about 25 μs/cm.

The behaviors within the decationizer means 7 of the various ionic species separated and eluted as indicated above will be described below with reference to FIG. 3A.

While the scavenger solution, HCl, is flowing as separated into $H^+$ and $Cl^-$ through the scavenger solution compartment 76, it continues an action of substituting the $H^+$ for the cation-exchange group in the wall of the tube 71 made of the cation-exchange composition. During the presence of this action, the tube 71 constitutes an H form cation-exchange composition. When the eluant solution, NaOH, containing the various ionic species separated in and eluted from the separation column 4 comes into contact with the wall of the tube 71 in that state, there ensures a reaction represented by the formula (2) wherein the $Na^+$ present in the eluant solution exchanges itself for the $H^+$ in the wall of the tube 71 and the eluant solution is converted into water.

$$NaOH + Resin\text{-}H^+ \rightarrow H_2O + Resin\text{-}Na^+ \qquad (2)$$

As a consequence of this reaction, the electric conductivity of the eluant solution falls from about 210 μs/cm (the conductivity of the 0.002 N NaOH) to the order of 10 to 15 μs/cm (the conductivity of water approximating that of pure water) and the background of the chromatogram is diminished to a great extent. As the $Na^+$ enters the wall of the tube 71, the $Na^+$ concentration in the scavenger solution falls to near zero. The $Na^+$ in the wall of the tube, therefore, diffuses through the wall and migrates in the direction of the scavenger solution and reaches the wall surface in contact with the scavenger solution. Since the scavenger solution is formed of an HCl solution of relatively high concentration, there ensues a reaction represented by the formula (3) below. Thus, the Na$^{30}$ in the wall of the tube 71 is exchanged for the H$^+$ in the scavenger solution. (This reaction is identical with the reaction which is observed during the regeneration of an ion-exchange resin involved in the operation of an apparatus for the production of pure water by use of the ion-exchange resin.)

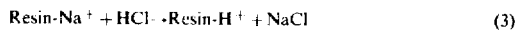

$$\text{Resin-Na}^+ + \text{HCl} \rightarrow \text{Resin-H}^+ + \text{NaCl} \qquad (3)$$

In the same manner, cations other than the H$^+$ which are present in the aforementioned eluant solution migrate by diffusion through the wall of the tube 71 and eventually reach the wall surface in contact with the scavenger solution. The cations which have migrated through the tube wall and reach the surface are entrained by the scavenger solution moving in a continuous flow and are discharged out of the compartment 76. Thus, these cations never accumulate within the compartment 76. As the result, the speed of diffusion of such cations within the wall of the tube 71 is not lowered. In effect, the tube 71 which is made of the cation-exchange composition is always regenerated (i.e. retained in the H form) by the scavenger solution.

The anionic species which are separated in and eluted from the separation column 4 enter the eluant solution compartment 75 in the form of salts, NaCl, NaNO$_3$, and Na$_2$SO$_4$, as described above, and undergo the reactions represented by the formulas (4), (5), and (6) below.

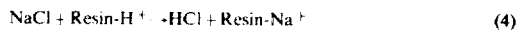
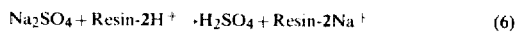

$$\text{NaCl} + \text{Resin-H}^+ \rightarrow \text{HCl} + \text{Resin-Na}^+ \qquad (4)$$

$$\text{NaNO}_3 + \text{Resin-H}^+ \rightarrow \text{HNO}_3 + \text{Resin-Na}^+ \qquad (5)$$

$$\text{Na}_2\text{SO}_4 + \text{Resin-2H}^+ \rightarrow \text{H}_2\text{SO}_4 + \text{Resin-2Na}^+ \qquad (6)$$

Figure 6:
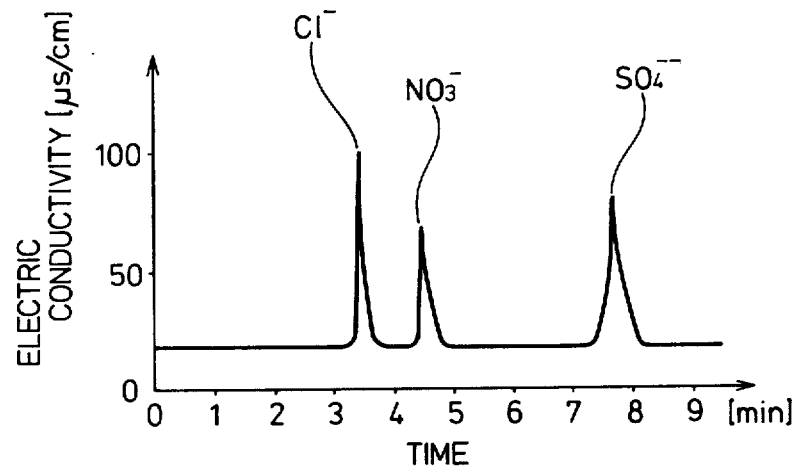
FIG. 6 is a diagram showing a typical chromatogram of the effluent at the outlet of the diffusion type decationizer means in the typical ion chromatograph for the analysis of anions according to the present invention.

Since the eluant solution, NaOH, is converted to H$_2$O by the reaction of the formula (2) and, at the same time, the various ionic species are converted from the Na form to the acid form by the reactions of the formulas (4) through (6), the chromatogram of the solution which was flowed through the decationizer means 7 shows a very low, stable base line as illustrated in FIG. 6. In the chromatogram, the peak forms of the cations are no longer present and the peak forms of the anionic species are enlarged. (Generally, the conductivity of a solution is higher in an acid form than in a salt form.) In effect, therefore, in the decationizing means, the electric conductivity levels of the anionic species are amplified.

The embodiment given above has been described as involving a construction incorporating a separation column packed with a strongly basic anion-exchange resin. The invention is not limited to this embodiment. Optionally, it may be embodied in a construction using a separation column packed with a weakly basic anion-exchange resin. Further, generally the kind of the eluate solution varies with the kind of the separation column employed. In the case of the decationizer means described above, if a mixed solution of 0.003 M Na$_2$CO$_3$ and 0.0024 M NaHCO$_3$, a solution of 0.004 M potassium hydrogen phthalate, or a solution of 0.001 M phthalic acid, for example, is used as the eluant solution in the place of the NaOH solution, it similarly fulfils the function of exchanging its cation of the eluant solution for H$^+$. Thus, the present invention places no limit upon the kind of the eluant solution used. Nor does it limit the structure of the decanionizer means to that of a double-wall tube described above. What is important is that the means should be provided with two compartments, i.e. an eluant solution compartment and a scavenger solution compartment, which share one wall made of a cation-exchange composition. For example, the means may be formed by dividing the interior of a box-shaped container with a cation-exchange membrane into two compartments and using one of them as an eluant solution compartment and the other as a scavenger solution compartment. The pump to be used for delivering the scavenger solution under pressure is not an essential requirement. For example when the scavenger solution reservoir is installed at a level higher than the decationizer means and, therefore, the delivery of the scavenger solution may be effected by the difference in liquid level without requiring a pump.

Now, another aspect of the present invention embodied in an ion chromatograph for the analysis of cations will be described.

Figure 4:
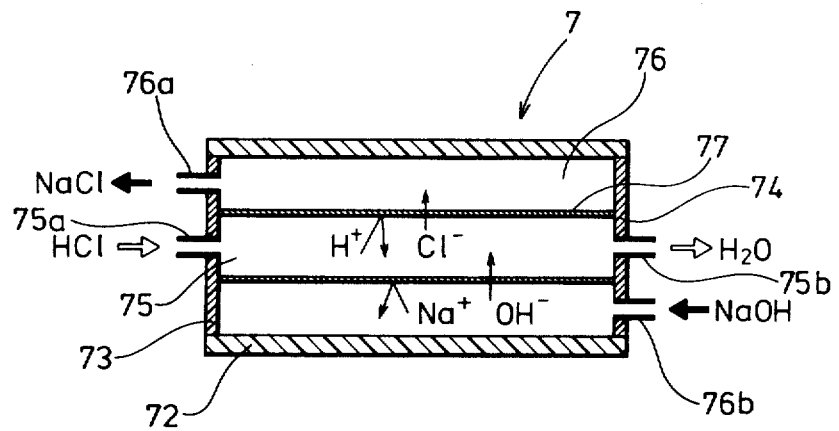
FIG. 4 is an explanatory diagram illustrating the construction of a diffusion type deanionizer means using an anion-exchange composition in the typical analytical apparatus of the present invention.

The configuration of flow paths in the ion chromatograph for the analysis of cations is similar to that of flow paths in the ion chromatograph for the analysis of anions illustrated in FIG. 2, except for the following points. The eluant solution reservoir 1 is a reservoir for storing a solution of 0.002 N HCl, the separation column 4 is a column packed with a strongly acidic cation-exchange resin having a low ion-exchange capacity, the diffusion type means 7 for the removal of ions of the opposite sign is a deanionizer means which is formed, as illustrated in FIG. 4, of an eluant solution compartment 75 and a scavenger solution compartment 76 and a wall 77 made of an anion-exchange composition and shared by the two compartments, and the scavenger solution reservoir 8 is a reservoir for storing a solution of 0.1 N NaOH (or KOH).

The ion chromatograph for the analysis of cations is operated as described below.

The eluant solution, 0.002 N HCl, is forwarded by the pump 2 at a flow volume of about 2.0 ml/min. through the sample injection means 3, the separation column 4, and eluant solution compartment 75 of the deanionizer means 7, and the cell of the conductivity meter 6 to the reservoir 10. The scavenger solution, 0.1 N NaOH, is forwarded by the pump 9 at a flow volume of about 1 ml/min. through the scavenger solution compartment 76 of the deanionizer means 7 to the reservoir 11.

Figure 7:
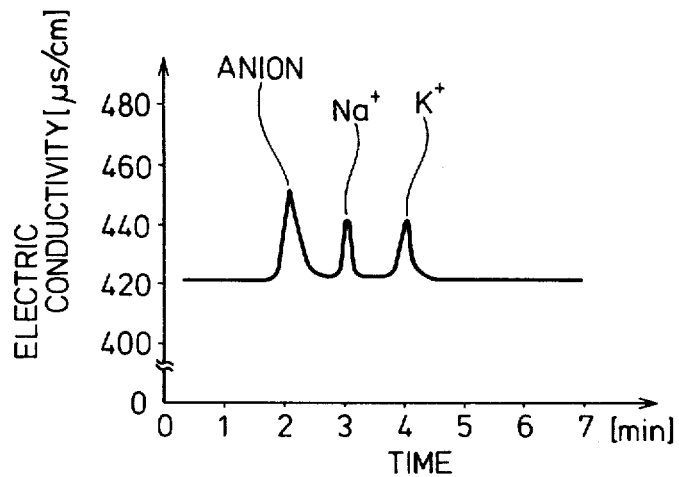
FIG. 7 is a diagram showing a typical chromatogram of the effluent at the outlet of the typical ion chromatograph for the analysis of cations according to the present invention.

Now, at the sample injection means 3, a sample solution 100 μl in volume containing 100 mg/liter (ppm) of Na$^+$ and 100 mg/liter (ppm) of K$^+$ is poured into the flow of the eluant solution at the sample injection means and forwarded to the separation column 4. In the separation column 4, the ionic species are separated. The chromatogram of the liquid at the outlet of the separation column 4 is as shown in FIG. 7. In this chromatogram, with the conductivity, about 420 μs/cm, of the 0.002 N HCl as the base line, the anion (Cl$^-$ where the ion paired with the cation of interest is Cl or Br$^-$ where the ion is Br, for example), and the cations Na$^+$ and K$^+$ appear in the order mentioned. Actually, the cationic species are bonded with the Cl$^-$ in the eluant solution to that Na$^+$ exists as NaCl and K$^+$ as KCl. Since these salts are eluted out as contained in the 0.002 N HCl, the change of conductivity at the peak of Na$^+$, for example is about 25 μs/cm.

The behaviors within the deanionizer means 7 of the various ionic species separated and eluted as indicated above will be described below with reference to FIG. 4.

While the scavenger solution, NaOH, is flowing as separated into Na+ and OH− through the scavenger solution compartment 76, it continues an action of substituting the OH− for the anion-exchange group in the wall of the tube 77 made of the anion-exchange composition. During the presence of this action, the tube 77 constitutes an OH form anion-exchange composition. When the eluant solution, HCl, containing the various ionic species separated in and eluted from the separation column 4 comes into contact with the wall of the tube 77 in that state, there ensues a reaction represented by the formula (7) shown below wherein the Cl− present in the eluant solution exchanges itself for the OH− in the wall of the tube 77 and the eluant solution is converted into water.

$$HCl + \text{Resin-OH}^- \rightarrow H^2O + \text{Resin-Cl}^- \quad (7)$$

As a consequence of this reaction, the electric conductivity of the eluant solution falls from about 420 μs/cm (the conductivity of the 0.002 N HCl) to the order of 10 to 15 μs/cm (the conductivity of water approximating that of pure water) and the background of the chromatogram is diminished to a great extent.

As the Cl− enters the wall of the tube 77, the Cl− concentration in the scavenger solution falls to near zero. The Cl− in the wall of the tube, therefore, diffuses through the wall and migrates in the direction of the scavenger solution and reaches the wall surface in contact with the scavenger solution. Since the scavenger solution is formed of an NaOH solution of relatively high concentration, there ensues a reaction represented by the formula (8) below. Thus, the Cl− in the wall of the tube 77 is exchanged for the OH− in the scavenger solution. (This reaction is identical with the reaction which is observed during the regeneration of an ion-exchange resin involved in the operation of an apparatus for the production of pure water by use of the ion-exchange resin.)

$$\text{Resin-Cl}^- + NaOH \rightarrow \text{Resin-OH}^- + NaCl \quad (8)$$

In the same manner, the other anions than the Cl− which are present in the aforementioned eluant solution migrate by diffusion through the wall of the tube 77 and eventually reach the wall surface in contact with the scavenger solution. The anions which have migrated through the tube wall and reach the surface are entrained by the scavenger solution moving in a continuous flow and discharged out of the compartment 76. Thus, these anions are never accumlated within the compartment. As the result, the speed of diffusion of such anions within the wall of the tube 77 is not lowered. In effect, the tube 77 which is made of the anion-exchange composition is always regenerated (i.e., retained in the OH form) by the scavenger solution.

The cationic species which are separated in and eluted from the separation column 4 enter the eluant solution compartment 75 in the form of salts, NaCl and KCl, as described above, and undergo the reactions represented by the formulas (9) and (10) below.

$$NaCl + \text{Resin-OH}^- \rightarrow NaOH + \text{Resin-Cl}^- \quad (9)$$

$$KCl + \text{Resin-OH}^- \rightarrow KOH + \text{Resin-Cl}^- \quad (10)$$

Figure 8:
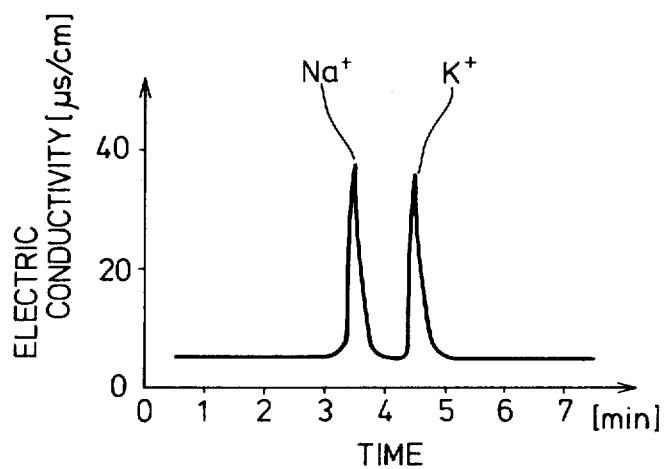
FIG. 8 is a diagram showing a typical chromatogram of the effluent at the outlet of the diffusion type deanionizer means in the typical ion chromatograph for the analysis of cations according to the present invention.

Since the eluant solution, HCl, is converted to $H_2O$ by the reaction of the formula (7) and, at the same time, the various ionic species are converted from the salt form to the hydroxide form by the reactions of the formula (9) and (10), the chromatogram of the solution which has flowed through the deanionizer means 7 shows a very low, stable base line as illustrated in FIG. 8. In the chromatogram, the peak forms of the anions are no longer present and the peak forms of the cationic species are enlarged. (Generally, the conductivity of a solution is higher in a hydroxide form than in a salt form.) In effect, therefore, in the deanionizer means, the electric conductivity levels of the cationic species are amplified.

Now, the operation of the apparatus using a sample solution containing Be, Zn, Cu, Cd, etc. will be described. The system using the conventional BSC has been unable to measure the concentrations of these ionic species.

Even with the apparatus of FIG. 2, when an effort is made to convert the HCl wholly into $H_2O$, it sometimes occurs that the aforementioned ionic species will convert themselves into hydroxides of low levels of solubility and settle to the bottom even to the extent of rendering the measurement impracticable. In this case, however, the trouble may be precluded by suitably adjusting the concentration of the scavenger solution or the length of the flow path of the eluant solution compartment in the deanionizer means (the length of the tube 77). Thus, the apparatus of FIG. 2 may be modified so as to become operative with sample solutions having Be, Zn, Cu, Cd, etc. as the ionic species of interest.

The foregoing embodiment has been described as involving a construction incorporating a separation column packed with a strongly acidic ion-exchange resin. This invention is not limited to this embodiment. Optionally, it may be embodied in a construction using a separation column packed with a weakly acidic cation-exchange resin. Even the deanionizer means to be used in the present invention need not be limited in its design. As already pointed out above with respect to the decationizer means, the deanionizer means may be formed by dividing the interior of a box-shaped container into two compartments with an anion-exchange membrane.

Now, an electrodialysis type deionizer means (hereinafter referred to as EBS) which uses, as its principal component, the same ion-exchange composition as in the foregoing embodiment will be described.

Figure 9A:
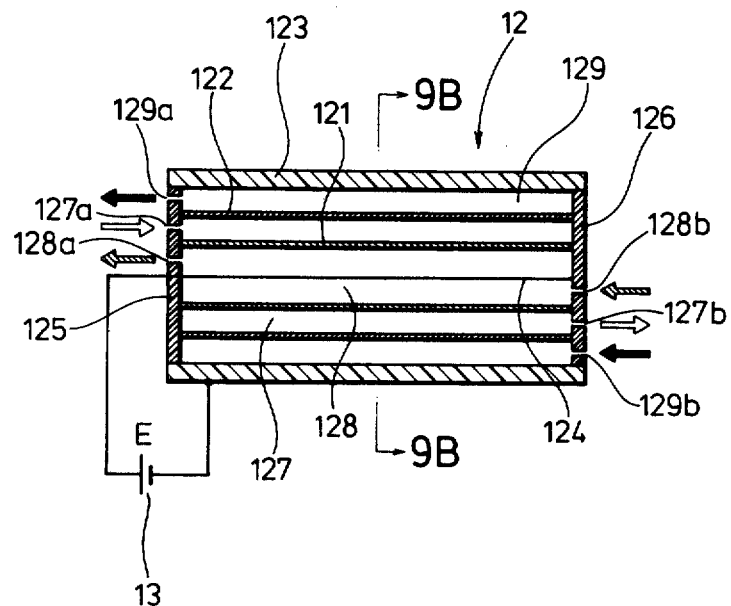
FIG. 9A is an explanatory diagram illustrating the construction of an electrodialytic decationizer means using a cation-exchange composition.
Figure 9B:
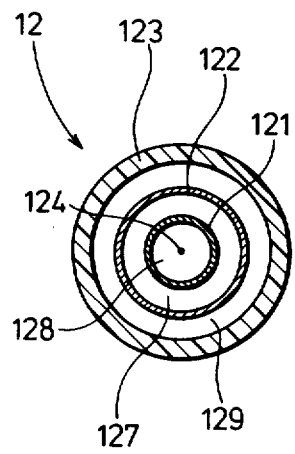
FIG. 9B is a cross section taken along the line 9B—9B in the diagram of FIG. 9A.

FIG. 9A illustrates the EBS in a cross section taken along the axial direction, and FIG. 9B is a cross section taken along the line 9B—9B of the diagram of FIG. 9A.

A cell 12 intended to serve as the EBS has a construction wherein a three-wall tube is formed by using a tube 121 made of a cation-exchange composition and enclosing an anode 124 of platinum wire, a tube 122 made of a cation-exchange composition and encircling the tube 121, a tube 123 made of stainless steel and encircling the tube 122, and interposing suitable tubular spaces between the tubes. The opposite open ends of the three-wall tube are closed with lids 125 and 126 both made of an insulating material to give rise therein to an eluant solution compartment 125, an anolyte solution compartment 128, and a catholyte solution compartment 125 independently of one another, and holes 127a, 127b, 128a, 128b, 129a, and 129b are formed to establish communication between the interiors of these compartments and the ambient air. The liquid eluted from the separation column flows in the direction of the hole 127a, through the eluant solution compartment 127, and the hole 127b. The anolyte solution delivered under pressure by the pump is forwarded in the direction of the hole 128b, through the anolyte solution compartment 128, and the hole 128a. The catholyte solution delivered under pressure by the pump is forwarded in the direction of the hole 129b, through the anolyte solution compartment 129, and the hole 129a. The direction in which the eluant solution flows is opposite the direction in which the anolyte solution and the catholyte solution are forwarded.

A DC voltage generator 13 connected between the tube 123 and the anode 124 generates the potential E upon the tube 23 serving as the cathode.

The operation of the analytical apparatus using the EBS the construction described above in the place of the diffusion type deionizer means of FIG. 2 will now be described.

The diluant solution, 0.002 N NaOH, is delivered by the pump 2 at a flow volume of about 2.0 ml/min. through the sample injection means 3, the separation column 4, the eluant solution compartment 77 of the EBS cell 7, the cell of the conductivity meter 6, and the reservoir 13a. The anolyte solution, 0.002 N HCl, is forwarded by an anolyte solution pump (not shown) at a flow volume of about 1 ml/min. through the anolyte solution compartment 128 of the EBS cell 12 to a storage reservoir (not shown). Similarly, the catholyte solution, 0.002 N NaOH, is delivered by a catholyte solution pump (not shown) at a flow volume of about 1 ml/min. through the catholyte solution compartment 128 of the cell and a storage reservoir (not shown).

When, under the same conditions as those of the aforementioned operation of the diffusion type decationizer means of FIG. 3A, the same sample solution containing the various anionic species is introduced through the sample injection means 3 and treated, the solution which has flowed through the EBS 12 provides a chromatogram shown in FIG. 6.

Thus the EBS 12, provides the same operation and effect as those obtainable with the diffusion type decationizer means. This is because the operation described below takes place in the EBS 12.

The operation of the EBS will be described with reference to FIG. 10.

Figure 10:
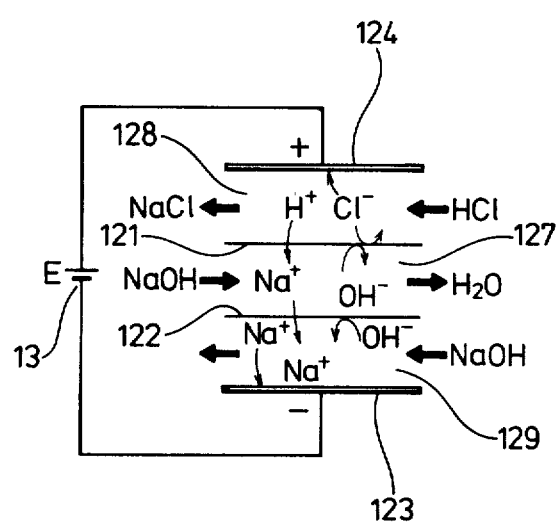
FIG. 10 is an explanatory diagram illustrating the operation of the electrodialytic decationizer means.

The numerical symbols used in FIG. 10 have the same meanings as those of FIG. 9A.

Owing to the potential E applied between the anode 124 and the cathode 123, the cations migrate in the direction of the cathode 123 and the anions in the direction of the anode 124. Because of the presence of the cation-exchange membrane 121, 122, however, the anions are not allowed to pass through the membranes while the cations are allowed to freely pass through the membranes and reach the cathode 123. While the NaOH in the eluant solution is passing, as separated into Na$^+$ and OH$^-$, through the eluant solution compartment 127, the Na$^+$ is allowed to pass through the cation-exchange membrane 122 and move on toward the cathode 123. In the meantime, from the anolyte solution compartment 128 through which the anolyte solution, HCl, is flowing, the H$^+$ is fed through the cation-exchange membrane 121 to the eluant solution compartment 127. By the reaction of the formula (11), the NaOH in the eluate solution is converted into H$_2$O and, consequently, the electric conductivity of the eluant solution is notably lowered.

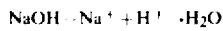

(11)

The various ionic species separated in and eluted from the separation column 4 enter the eluant solution compartment 127 in their respectively converted forms of NaCl, NaNO$_3$, and Na$_2$SO$_4$ as described above. Within this compartment, the salts undergo the reactions represented by the formulas (12), (13), and (14) shown below.

 (12)

 (13)

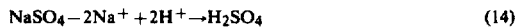 (14)

Since the NaOH in the eluant solution is converted into H$_2$O by the reaction of the formula (11) as described above, the electric conductivity of the eluant solution is notably lowered and the base line occurs at a very low, stable level. The chromatogram of the solution which has flowed through the EBS, therefore, is as shown in FIG. 6.

If, in the EBS 12, the anode 124 and the cathode 123 are both ideal electrodes, then no electrolysis of water occurs where the potential applied to the two electrodes is below 1.23 V but the reactions of the formulas (11) through (14) alone are allowed to proceed. If the potential E so applied is increased above the potential for the electrolysis of water, the reactions of the formulas (11) through (14) are caused to proceed with enhanced efficiency, although Cl$_2$ is generated at the anode 124 and H$_2$ at the cathode 123 respectively.

The kind of the eluant solution is variable with the kind of the separation column to be used. Even when a mixed solution of 0.003 M Na$_2$CO$_3$ and 0.0024 M NaHCO$_3$, a solution of 0.004 M potassium hydrogen phthalate, or a solution of 0.001 M phthalic acid is used as the eluant solution, the electric conductivity of the solution can be amplified just the same because the EBS is capable of performing the reaction of converting all the anionic species into the acid forms.

When the electrodyalysis type deionizer means described above has its main component formed of an anion-exchange composition and has its design modified so as to permit flow of required anolyte solution and catholyte solution, it can be utilized in an apparatus for the analysis of anionic species in a sample solution containing anionic species as those of the opposite sign.

As described above, the analytical apparatus of the present invention is so constructed that the removal of the ionic species of the opposite sign is effected by continuing the flow of the scavenger solution to the deionizer means formed of an ion-exchange composition of the opposite sign. Unlike the apparatus using the conventional BSC, this analytical apparatus can be operated without being interrupted for the regeneration of the BSC.

When the solution is passed through the means adapted for the removal of the ionic species of the opposite sign, the chromatogram of the solution at the outlet of this means has an amply low base line and shows ion peaks of interest at high levels. Thus, the detection on the electric conductivity meter is attained with notably enhanced sensitivity.

Further, the means for the removal of the ionic species of the opposite sign requires nothing to fill the eluant solution compartment, it has no possibility of destroying the peak forms in the chromatogram of the solution being passed therethrough.

We claim:

1. In a method for the chromatographic quantitative analysis of a sample solution containing at least one ionic species of interest paired with at least one ionic species of the opposite sign, said method including transporting a prescribed quantity of said sample solution with an eluant solution, introducing said solution into a separation column packed with an ion exchange resin to separate said ionic species of interest from said ionic species of the opposite sign, deionizing an eluate from said column and said eluant solution to remove said ionic species of the opposite sign therefrom, and measuring the electric conductivity of said eluate to thereby determine the concentration of said ionic species of interest in said sample solution, the improvement which comprises introducing said eluate into an inner passage of a deionizer having a single concentric double tubular construction, while a scavenger solution is introduced into an outer passage of said deionizer in a direction of flow opposite to that of said eluate in said inner passage, said inner passage being defined by a first tube of an ion exchange composition and provided with an inlet and an outlet for said eluate, said outer passage being defined by a second tube of a liquid-tight material other than an ion exchange composition encircling said first tube in radially spaced apart relation therefrom, and provided with an inlet and an outlet for said scavenger solution, said inner and outer passages being arranged independently of each other and said inlets and outlets of each of said inner and outer passage communicating with the outside, fluidally connecting said outlet of said inner passage to a conductive meter, whereby said ionic species of the opposite sign is removed from said inner passage into said scavenger solution in said outer passage through the wall of said first tube without impairing the peak form of said ionic species of interest separated by said column.

2. A method set forth in claim 1, wherein said scavenger solution is a solution of an acid selected from the group consisting of hydrochloric acid and nitric acid, while said eluant solution is an alkaline solution.

3. A method as set forth in claim 2, wherein said alkaline solution is selected from the group consisting of a solution of sodium hydroxide, a mixed solution of sodium carbonate and sodium hyrdrogen carbonate, a solution of potassium hydrogen phthalate and a solution of phthalic acid.

4. A method as set forth in claim 1, wherein said scavenger solution is a solution of sodium hydroxide, while said eluant solution is a solution of hydrochloric acid.

5. In an apparatus for the chromatographic quantitative analysis of a sample solution containing at least one ionic species of interest paired with at least one ionic species of the opposite sign, said apparatus including:
a reservoir for an eluant solution;
means for forwarding said eluant solution under pressure;
means for sampling a prescribed quantity of said sample solution;
a separation column into which said sample solution is introduced with said eluant solution so that said ionic species of interest may be separated from said ionic species of the opposite sign;
a deionizer into which an eluate is introduced from said column with said eluant solution so that said ionic species of the opposite sign may be removed from said eluate and said eluate solution; and
a conductivity meter for measuring the electric conductivity of said eluate introduced thereinto from said deionizer with said eluant solution, whereby the concentration of said ionic species of interest in said sample solution is determined,
the improvement which comprises:
said deionizer having a single concentric double tubular construction which comprises a first tube of an ion exchange composition, and a second tube of a liquid-tight material other than an ion exchange composition encircling said first tube in radially spaced apart relation therefrom, said first tube defining an inner passage having an inlet through which said eluate is introduced from said column, and an outlet connected fluidally to said conductivity meter, said second tube defining an outer passage about said first tube having an inlet through which a scavenger solution is introduced into said outer passage in a direction of flow opposite to that of the fluid in said inner passage, and an outlet through which said scavenger solution is discharged with said ionic species of the opposite sign removed from said fluid in said inner passage said inner and outer passages being arranged independently of each other and said inlets and outlets of each of said inner and outer passages communicating with the outside;
a reservoir for said scavenger solution; and
means for forcing said scavenger solution under pressure into said outer passage.

6. An apparatus as set forth in claim 5, wherein said scavenger solution is a solution of acid selected from the group consisting of hydrochloric acid and nitric acid which is fed to said deionizer from said reservoir for said scavenger solution through said inlet of said outer passage to said outer passage, while said eluant solution is an alkaline solution which is fed to said deionizer from said separation column through said inlet of said inner passage to said inner passage.

7. An apparatus as set forth in claim 6, wherein said alkaline solution is selected from the group consisting of a solution of sodium hydroxide, a mixed solution of sodium carbonate and sodium hydrogen carbonate, a solution of potassium hydrogen phthalate and a solution of phthalic acid which is fed to said deionizer from said separation column through said inlet of said inner passage to said inner passage.

8. An apparatus as set forth in claim 5, wherein said scavenger solution is a solution of sodium hydroxide which is fed from said reservoir for said scavenger solution through said inlet of said outer passage to said outer passage, while said eluant solution is a solution of hydrochloric acid which is fed to said deionizer from said separation column through said inlet of said inner passage to said inner passage.

* * * * *